United States Patent [19]
Krasner et al.

[11] Patent Number: 5,337,435
[45] Date of Patent: Aug. 16, 1994

[54] AUTOMATIC TOOTHBRUSH

[76] Inventors: Janet H. Krasner; Paul R. Krasner, both of 285 Maugers Mill Rd., Pottstown, Pa. 19464

[21] Appl. No.: 946,656

[22] Filed: Sep. 18, 1992

[51] Int. Cl.$^5$ .................... A61C 17/16; A46B 13/02
[52] U.S. Cl. ............................ 15/23; 15/22.1; 15/28
[58] Field of Search ............... 15/22.1, 23, 24, 28, 15/29, 146; 128/62 A

[56] References Cited

U.S. PATENT DOCUMENTS

| | | | |
|---|---|---|---|
| 1,620,330 | 3/1927 | Douglass | 15/146 |
| 2,257,709 | 9/1941 | Anderson . | |
| 2,583,886 | 1/1952 | Schlegel . | |
| 2,628,377 | 2/1953 | Cockriel . | |
| 3,129,449 | 4/1964 | Cyzer . | |
| 3,163,874 | 1/1965 | Bauer . | |
| 3,398,421 | 8/1968 | Rashbaum | 15/167.2 |
| 3,535,047 | 10/1970 | Vireno . | |
| 4,224,710 | 9/1980 | Solow | 15/22.1 |
| 4,237,574 | 12/1980 | Kelly et al. . | |
| 4,429,434 | 2/1984 | Sung-shan . | |
| 4,450,599 | 5/1984 | Scheller et al. | 15/22.1 |
| 4,538,315 | 9/1985 | Barth | 15/22.1 |
| 4,698,869 | 10/1987 | Mierau et al. . | |
| 4,709,438 | 12/1987 | de Tavares . | |
| 4,788,734 | 12/1988 | Bauer . | |
| 5,177,827 | 1/1993 | Ellison | 15/22.1 |

Primary Examiner—Edward L. Roberts
Attorney, Agent, or Firm—William H. Eilberg

[57] ABSTRACT

An automatic toothbrush enables a user to brush all teeth of an arch simultaneously. A toothbrush portion includes a set of brushes arranged in an arc shaped to coincide with the shape of the user's mouth. The toothbrush includes side brushes for brushing the sides of the user's teeth, and occlusal brushes for brushing the biting surfaces of the teeth. All of the brushes are connected together by gears, so that rotation of one of the gears causes rotation of all of the brushes. The toothbrush includes a handle which contains a motor, the motor being connected to a drive shaft which engages one of the gears. The toothbrush also includes a display screen which is connectable to the handle, and which provides educational material or entertainment to the user while the toothbrush is in use. Also, the display screen may supply feedback to the user concerning the amount of plaque remaining on the teeth, or concerning some other aspect of the quality of the brushing

20 Claims, 8 Drawing Sheets

AUTOMATIC TOOTHBRUSH

BACKGROUND OF THE INVENTION

This invention relates to the field of toothbrushes, and provides an automatic toothbrush which can brush an entire arch of a user's teeth simultaneously.

The best known means of maintaining dental health is to brush the teeth regularly and thoroughly. Regular brushing reduces the incidence of tooth decay. Also, brushing and flossing reduce the accumulation of plaque, which is known to cause periodontal disease. Although the danger associated with accumulation of plaque has become widely publicized in recent years, most persons, especially children, the handicapped, and the elderly, still tend not to brush properly or sufficiently. Brushing the teeth with a conventional toothbrush is tedious, and many users do not brush for sufficiently long periods or in a correct direction. Moreover, users of conventional toothbrushes have no reliable way of knowing whether their brushing has been effective in removing plaque and other substances from the teeth.

One solution to the above problems is to use a powered toothbrush. An example of a powered toothbrush is given in U.S. Pat. No. 2,628,377. The latter patent discloses a device having a plurality of rotating brushes which clean an entire row of the user's teeth simultaneously.

U.S. Pat. No. 3,163,874 shows another toothbrush which is capable of cleaning all the user's teeth simultaneously. However, the toothbrush of the latter patent is not mechanized. Instead, the brush elements are stationary, and the user cleans his or her teeth by repeatedly biting down on the brush.

U.S. Pat. No. 3,129,449 discloses still another toothbrush having a plurality of oscillating and rotating brush elements.

The present invention provides an automatic toothbrush which is an improvement over the devices of the prior art. The present invention permits the user to brush substantially all of an entire arch of teeth simultaneously, with a powered brushing mechanism. The toothbrush of the present invention may also include a display screen which captures the attention of the user, and which inherently encourages the user to brush correctly and for longer periods of time than is customary with conventional toothbrushes.

SUMMARY OF THE INVENTION

The automatic toothbrush of the present invention includes a first set of brushes, arranged in an arc which generally follows the arc of the teeth, the brushes of the first set being intended to brush the sides of the teeth. A second set of brushes is arranged in a similar arc, the brushes of the second set being intended to brush the occlusal (biting) surfaces of the teeth. Both the brushes of the first set and the brushes of the second set are attached to a housing.

The brushes of both sets are rotatable, and all of the brushes are connected to gears or their equivalents. The brushes of the first set are geared together so that rotation of one brush causes rotation of all brushes of that set. Similarly, the brushes of the second set are geared together so that rotation of one brush causes rotation of all. At least one transfer gear connects the gears of the brushes of the first and second sets, so that rotation of one brush of the first set also causes rotation of all the brushes in the apparatus.

A power source, such as a motor, turns a drive shaft which is connected to a driving gear. The driving gear engages one of the gears which is attached to a brush of the first set. When power is applied, the brushes of the first set rotate. Simultaneously, the brushes of the second set also rotate, because of the afore-mentioned gearing arrangement. Thus, all of the brushes rotate at once. The brushes are spring-biased so that they tend to push against the teeth. The brushes therefore clean an entire arch of a user's teeth simultaneously. Because the brushes are spring-biased, the toothbrush can fit a wide variety of users.

The housing preferably has a double wall, including an inner shell and an outer shell. The brushes are disposed within, and affixed to, the inner shell. The inner shell is preferably removable from the outer shell. The brushes can therefore be removed from the outer shell and a new assembly of brushes can be inserted into the same outer shell. Thus, the same housing and driving mechanism can be used with brushes belonging to different users. Alternatively, the handle which supports the shell can be designed to come apart, so that an entirely new shell can be attached to the handle.

The invention also includes means for providing entertainment, education, and/or feedback to the user. The drive shaft is disposed within a handle which can also support a display screen. The screen is oriented so that it is plainly visible to the user while the brush is inserted in the user's mouth. The screen can display entertainment or instruction, e.g. from a program stored on a magnetic medium or a microprocessor or equivalent. Alternatively, the screen can display information on how well the user is brushing. For example, sensors disposed within the shell can determine how much plaque remains on the teeth, and can display this information on the screen, to tell the user whether more brushing is necessary.

It is therefore an object of the invention to provide an automatic toothbrush.

It is another object of the invention to improve the accuracy of brushing of the teeth.

It is another object to make the brushing of the teeth more enjoyable.

It is another object to provide an apparatus which encourages children to brush their teeth more regularly.

It is another object to provide a powered apparatus which brushes all of the teeth simultaneously.

It is another object to provide an automatic toothbrush which entertains or instructs the user while the user's teeth are being brushed.

It is another object to provide an automatic toothbrush which is capable of providing feedback to a user on how much brushing is still required, and/or on the efficacy of the user's brushing technique.

Other objects and advantages of the invention will be apparent to those skilled in the art, from a reading of the following brief description of the drawings, the detailed description of the invention, and the appended claims.

DETAILED DESCRIPTION OF THE INVENTION

Figure 1:
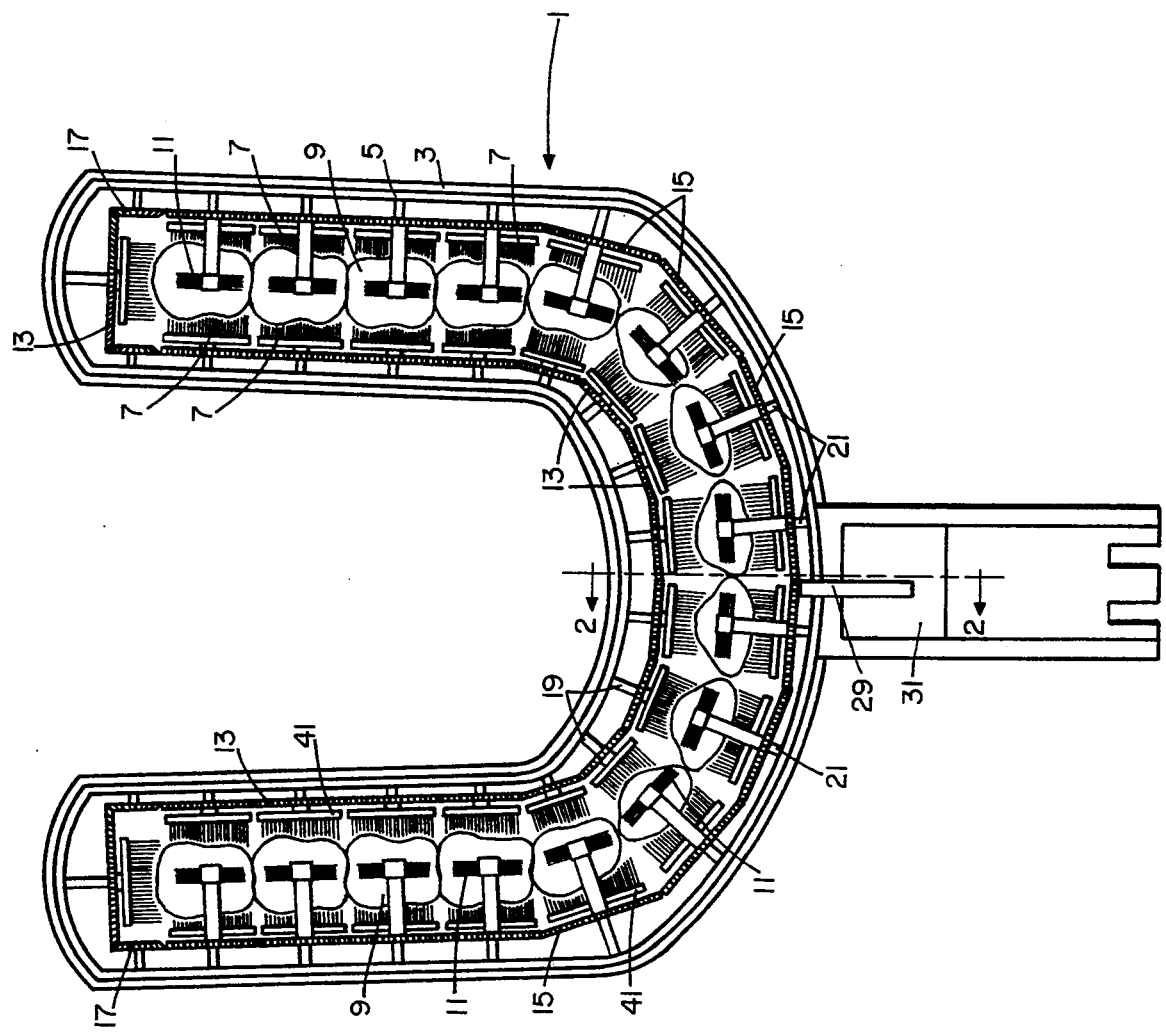
FIG. 1 is a plan view, partially in cross-section, showing the toothbrush of the present invention, as fitted over and around a set of teeth.
Figure 2:
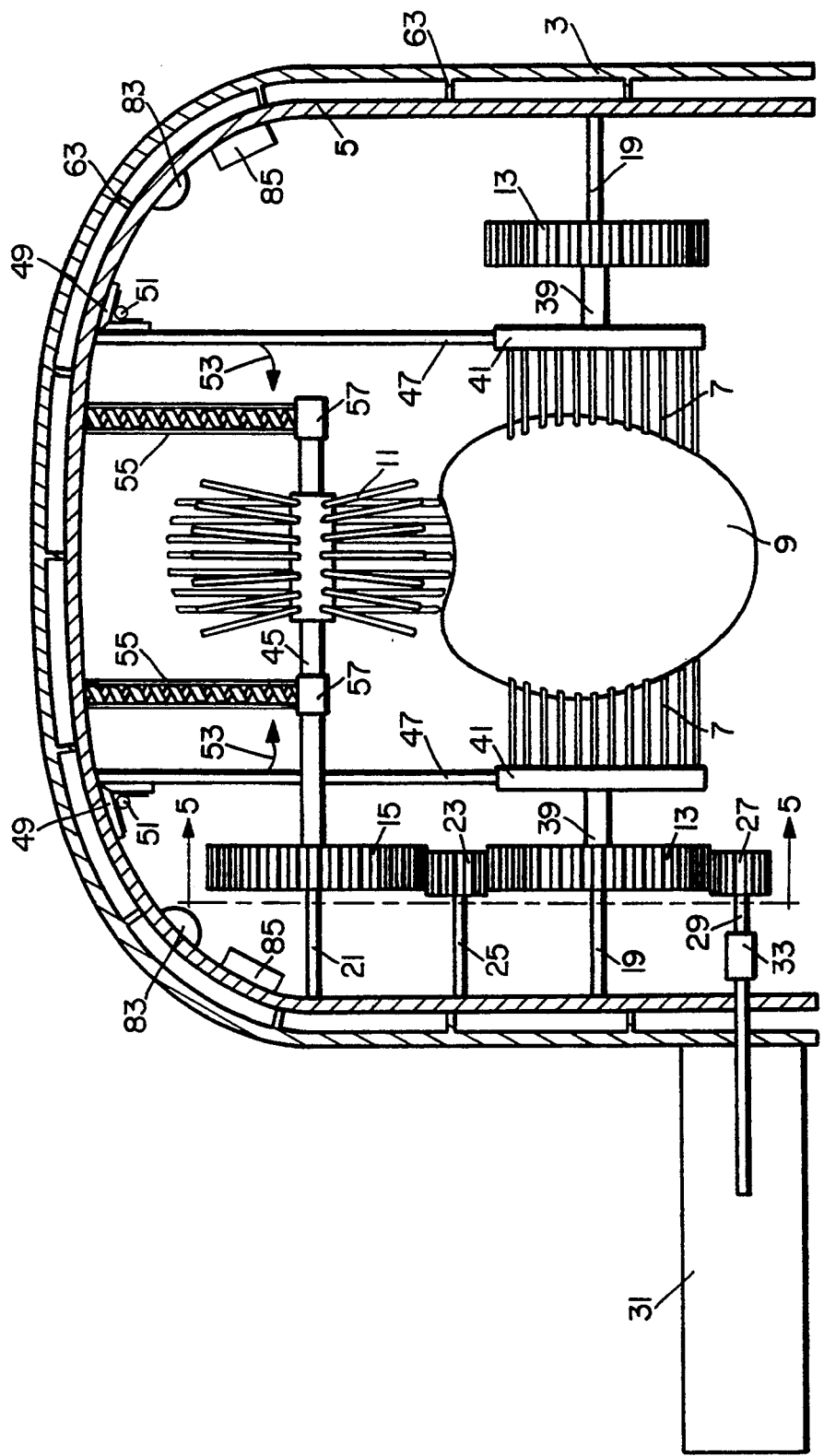
FIG. 2 is a cross-sectional view taken along the line 2—2 of FIG. 1, showing a pair of representative side brushes and an occlusal brush, and their respective gearing arrangements.

The present invention includes a toothbrush which can clean an entire arch of the user's teeth simultaneously, and which can be used with or without a display device for providing entertainment and/or information to the user. FIGS. 1 and 2 show the basic structure of the toothbrush portion, without the display device.

FIG. 1 shows toothbrush 1 housed in a casing which is defined by outer shell 3 and inner shell 5. The inner and outer shells are detachably affixed to each other, so that the inner shell can be removed from the outer shell when desired, as will be described below. The mechanical parts of the brush elements are connected to the inner shell only.

A plurality of side brushes 7 are disposed within inner shell 5. These side brushes are arranged in two generally parallel arcs, the arcs being shaped to correspond approximately to the shape of a user's mouth. There is a larger, outer arc and a smaller, inner arc. Thus, the side brushes are arranged so that they can engage the sides of the user's teeth. For convenience of illustration, FIGS. 1 and 2 show teeth 9, which of course do not form part of the invention.

The toothbrush also includes a plurality of occlusal brushes 11 which are disposed to brush the occlusal surfaces of the teeth, i.e. the surface farthest from the root of the tooth, and the surface which does the biting.

The side brushes 7 are connected to gears 13, and the occlusal brushes 11 are connected to gears 15. In FIG. 1, the gears connected to the side brushes which lie along the larger, outer arc are not visible because they are hidden by gears 15. However, FIG. 2 clearly shows the gears 13 disposed on either side of tooth 9.

Gears 13 engage each other such that rotation of one of the gears causes rotation of all of the gears. Rotational motion is transmitted around corners by suitable bevel gears 17, and is transmitted along curves by proper choice of the diameter, orientation, and shape of tooth of each gear, in a conventional manner. The gears 13 are connected to inner shell 5 by support members 19. The support members are non-rotating; the gears rotate relative to the support members. Similarly, gears 15 are connected to the inner shell by support member 21.

Figure 5:
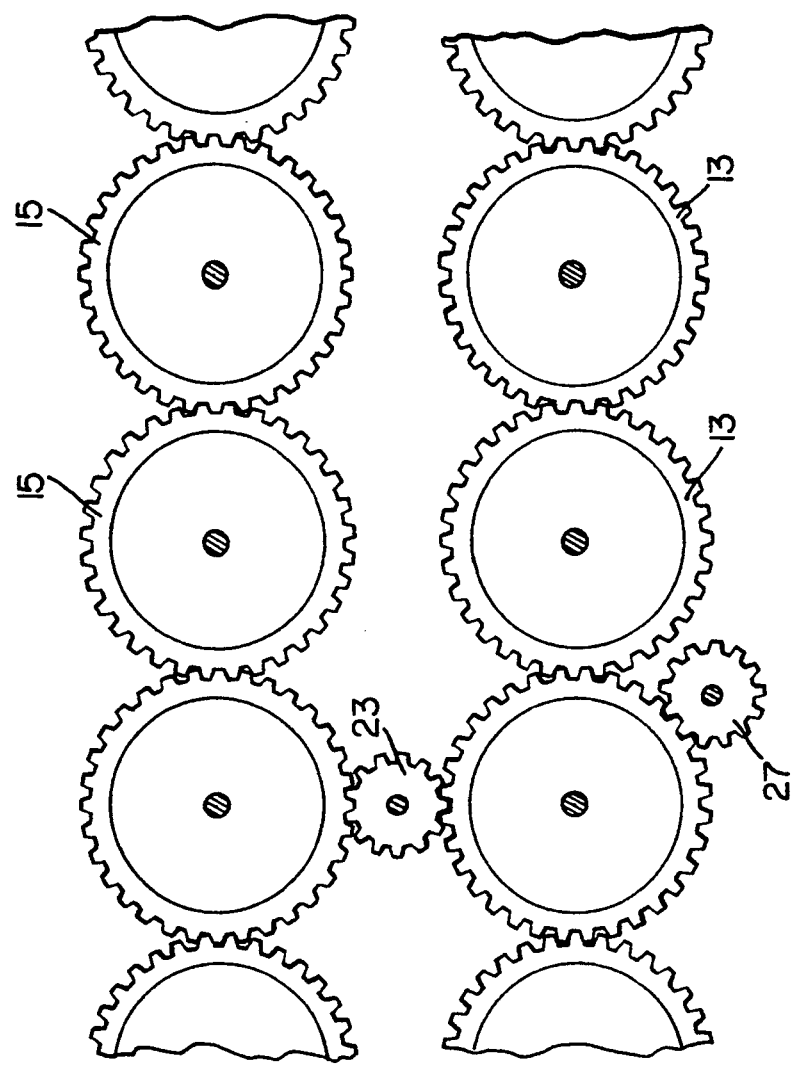
FIG. 5 is a fragmentary cross-sectional view, taken along the line 5—5 of FIG. 2, showing the gears which drive the side brushes and the top brushes of the toothbrush.

One or more transfer gears 23 connect gears 15 and gears 13. Each transfer gear is affixed to the inner shell by support member 25. There may be several transfer gears, located at various places along the arc of the toothbrush. FIG. 5, which is a cross-section taken along the line 5—5 of FIG. 2, shows the arrangement of the gears. Transfer gear 23 connects gears 13 to gears 15, such that gears 15 rotate when gears 13 rotate.

The entire ensemble of gears is driven by drive gear 27. The drive gear is mounted on drive shaft 29 which is connected to handle 31 of the toothbrush. The drive shaft extends through suitable openings in the inner and outer shells, to that the shaft can be removed and replaced. The shaft is preferably formed in two sections which are joined by coupling 33. The sections of the shaft can thus be uncoupled when it is desired to separate the drive shaft from the toothbrush.

Alternatively, one can design the handle so that it comes apart into two pieces, with a corresponding break in the drive shaft. Thus, the entire U-shaped structure, which includes the shells and brushes, can be detached from the handle, and a substantially identical structure can be substituted. The handle and drive shaft can be separated and reattached by using suitable male and female connectors (not shown). In other words, the U-shaped shell and brush assembly could be detached from the handle in the same manner in which dental drills are attached and detached from their handles and drive means, in the prior art. The specific structure for removably connecting the U-shaped structure from the handle does not itself form part of the present invention.

Figure 6:
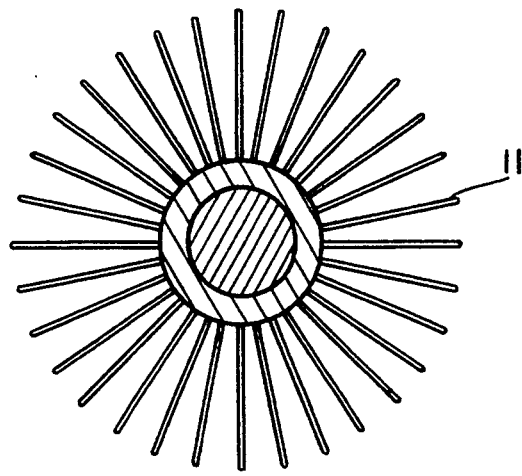
FIG. 6 is a cross-sectional view, taken along the line 6—6 of FIG. 10, showing one of the top brushes of the toothbrush of the present invention.

The structure of each of the occlusal brushes 11 is illustrated both in FIG. 2 and FIG. 6. The shape and number of the bristles can be varied.

Figure 7:
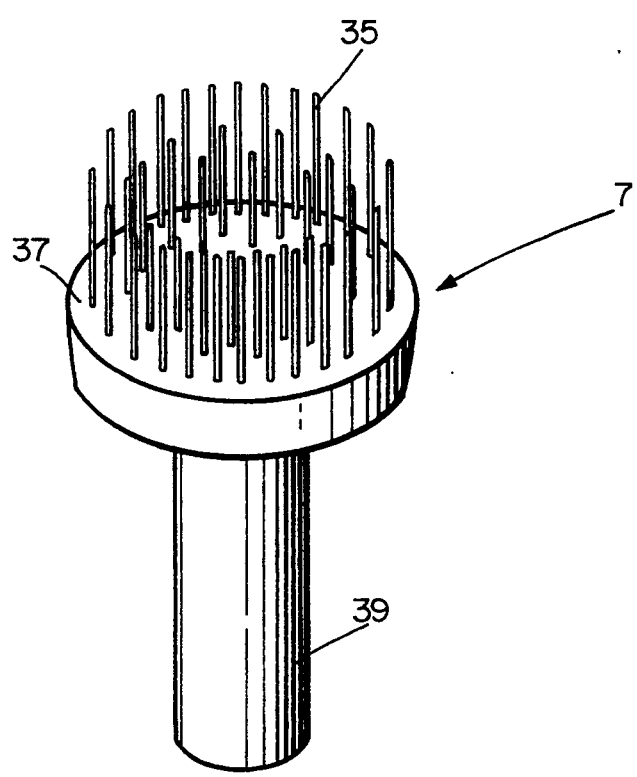
FIG. 7 is a perspective view of one of the side brushes of the toothbrush of the present invention.
Figure 8:
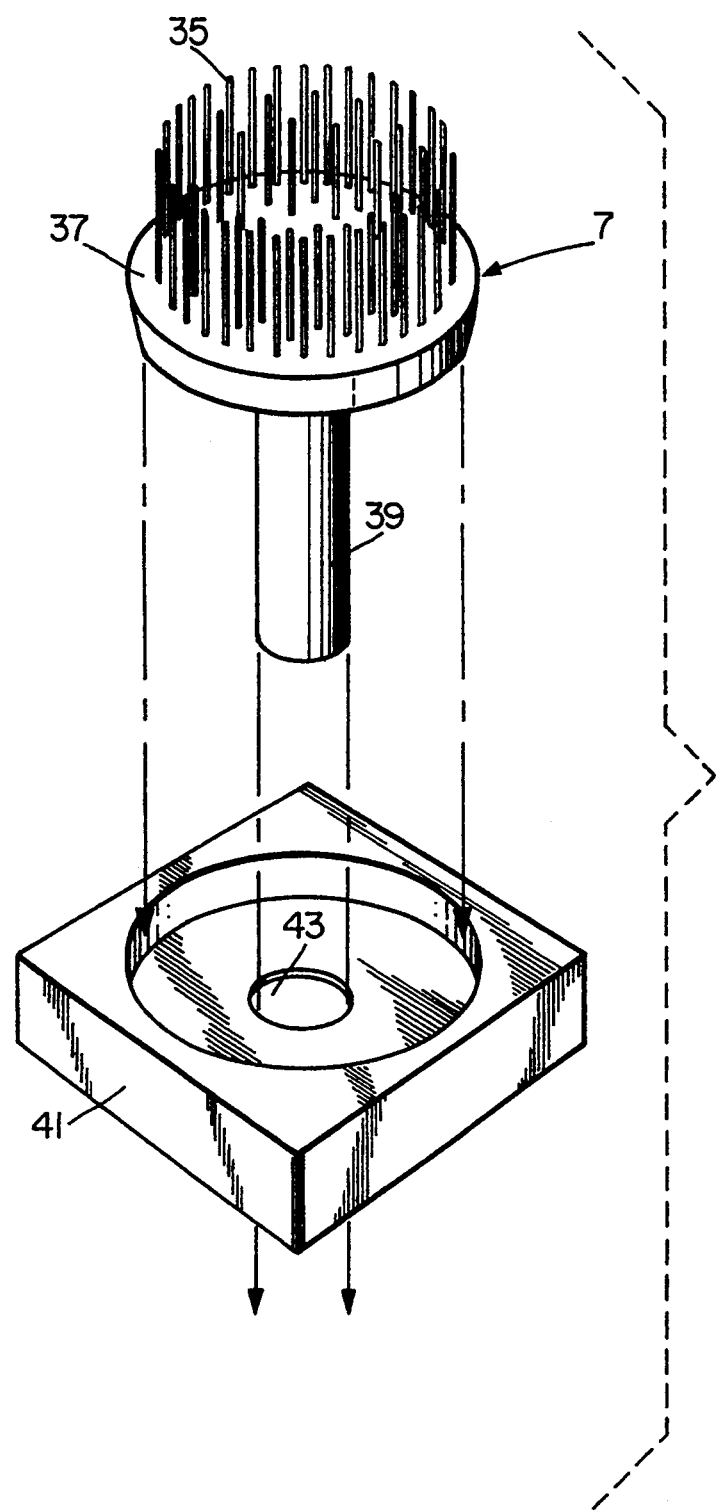
FIG. 8 is an exploded perspective view showing how the side brushes fit within recesses formed in holding plates.
Figure 10:
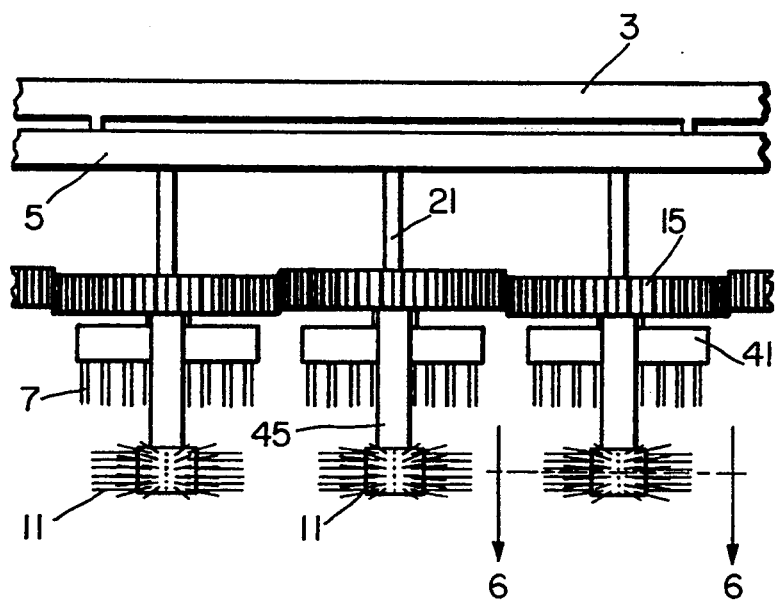
FIG. 10 is a fragmentary plan view of a portion of the toothbrush of the invention, showing three top brushes geared together, and also showing three of the side brushes.

FIGS. 7 and 8 illustrate the side brushes 7. FIG. 7 is a perspective view of the side brush 7 alone, showing its bristles 35, its base 37, and its support shaft 39. The support shaft is what is connected to gears 13. FIG. 8 shows that the side brushes are held within a mounting plate 41. The mounting plate has a generally circular recess which receives the similarly-shaped base. The mounting plates 41 are also shown in FIGS. 1, 2, and 10. Each mounting plate 41 has a hole 43 which receives support shaft 39. The mounting plate is stationary, while the support shaft is rotated by the gears 13. Rotation of the support shaft 39 causes rotation of the corresponding side brush 7.

As shown in FIG. 2, occlusal brushes 11 are mounted on shaft 45. Shaft 45 is rotated by gear 15, causing occlusal brush 11 to rotate also.

The mounting plates 41 for the side brushes 7 are supported within the inner shell 5 by support rods 47. As stated above, mounting plate 41 is non-rigid with support shaft 39; the shaft 39 rotates while the mounting plate 41 does not. The support rods are affixed to the inner shell by spring-biased hinges 49. Hinges 49 include springs 51 which are biased such that the hinges tend to move the rods 47 in the direction of arrows 53, i.e. towards the interior of the inner shell. Due to this biasing of the rods, the side brushes tend to push against teeth 9. The side brushes are thereby biased towards the teeth. It is this biasing effect which enables the toothbrush to fit firmly around the teeth of many different users. The brushes will naturally move towards the user's teeth until they press against the teeth.

The occlusal brushes 11 are held to the inner shell by springs 55. The springs are affixed to collars 57 which are fitted around shaft 45. The collars are non-rotatable with respect to shaft 45, and simply hold the shaft in the position shown, while allowing the shaft to rotate. The springs bias the occlusal brushes towards the open end of the shell, i.e. towards the tooth 9. Thus, the occlusal brushes are naturally biased towards the user's teeth, as are the side brushes.

Figure 9:
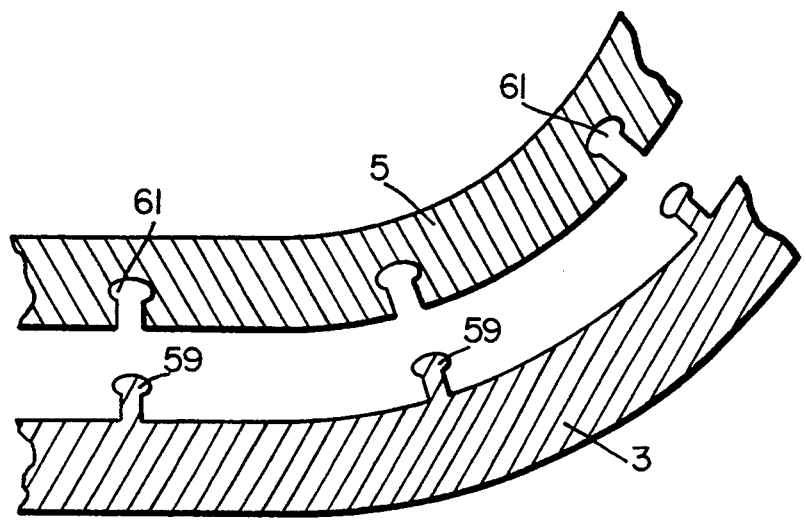
FIG. 9 is a fragmentary cross-sectional view of a portion of the inner and outer shell, showing a means for connecting one shell to the other.

FIG. 9 illustrates one means of connecting the inner and outer shells. Outer shell 3 includes a plurality of projections 59 which mate with recesses 61 in inner shell 5. The two shells can thus be snapped together. FIG. 1 shows the shells in the condition wherein they have been snapped together. FIG. 2 shows an alternative arrangement for holding the shells together. In FIG. 2, the shells are held together by struts 63, which may also be made removable. Except for the manner of holding the shells together, FIGS. 1 and 2 describe exactly the same structure, and therefore similar reference numerals have been used in both of these figures.

Figure 3:
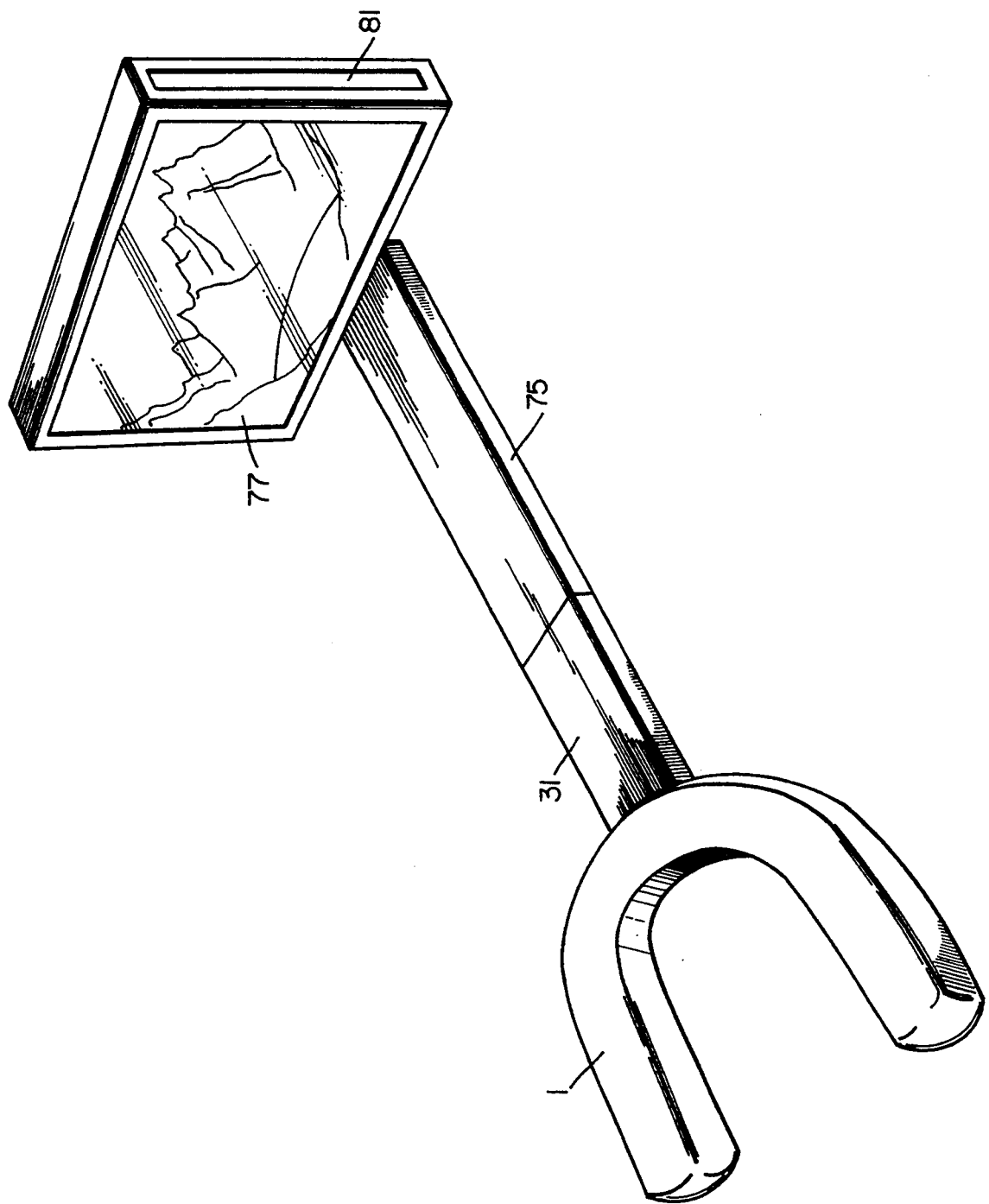
FIG. 3 is a perspective view showing the shell of the toothbrush attached to a display screen.
Figure 4:
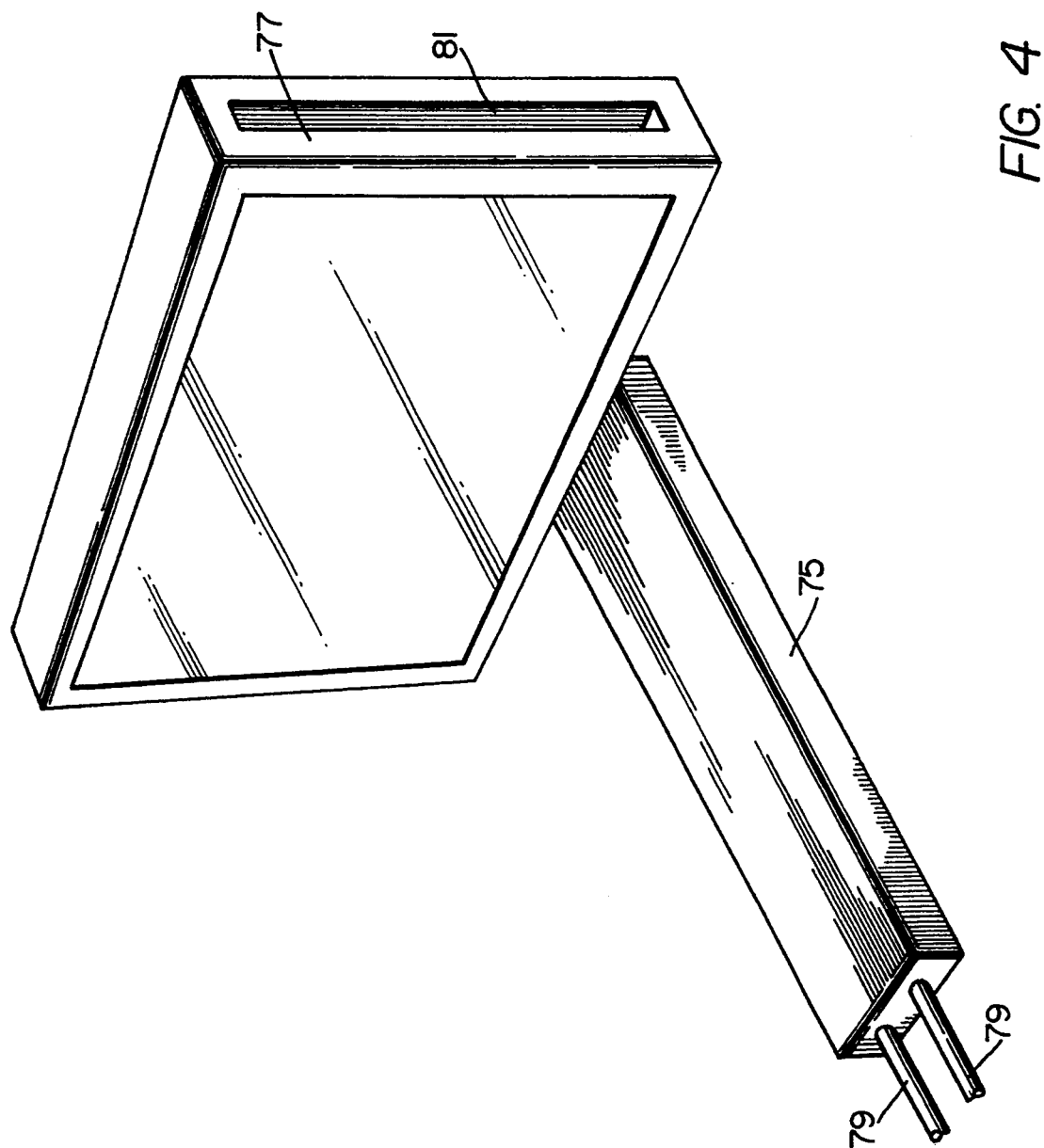
FIG. 4 is a perspective view of the display screen and its support arm, as detached from the toothbrush of the present invention.

FIGS. 3 and 4 show the display screen that is used with the toothbrush of the present invention. FIG. 3 shows the toothbrush 1 only in general outline; it is assumed that the toothbrush has the same structure shown in FIGS. 1 and 2. The toothbrush is connected to handle 31, and the handle is plugged into arm 75 which is connected to display screen 77. The screen can be used to provide entertainment to the user while the teeth are being cleaned. The display screen is oriented such that it faces the user while the teeth are being brushed. The subject matter displayed on the screen can be stored on a magnetic card (not shown) which can be inserted into slot 81. The subject matter could also be stored in a conventional tape cassette (not shown) which can be located within arm 75, or within handle 31, or even within the housing of the display screen. In another alternative, the subject matter can be stored in a microchip which can be located in any of the aforementioned positions. Power for the display can be derived from a battery (not shown) which is located within the handle or within the arm. The entertainment provided is not limited to images; the device can play music, through a conventional speaker (not shown) which can be mounted to the housing of the display screen.

As shown in FIG. 4, the display screen is detachable from the handle, and plugs into the handle through prongs 79. The display screen is preferably a liquid crystal or light-emitting diode (LED) display, although other display means can be used.

A motor (not shown) is disposed preferably within the handle. The motor causes drive shaft 29 to rotate, thereby causing all of the gears in the apparatus to move.

The subject matter shown on the display is not limited to entertainment. The display can also provide the user with information on how well the teeth have been brushed. For example, light sensors 85, shown in FIG. 2, can be provided in the interior of the toothbrush. Light from light-emitting diodes 83, or from another, equivalent source, is directed towards the teeth, and the light is reflected and collected by the sensors. The amount of plaque remaining on the teeth affects the intensity of the reflected light, so that the output of the sensors varies with the amount of plaque remaining on the teeth. The output of the sensors is connected to the display screen, by wires or other connections (not explicitly shown) that pass through the housing of the toothbrush and through handle 31, to the screen. Thus, the screen can display messages to the user, telling the user the location and/or quantity of plaque still remaining on the teeth. The screen can also be programmed to display graphically the amount of remaining plaque. Thus, the display screen can be used to provide feedback to the user concerning the quality of the brushing job. Of course, the toothbrush of the present invention can also be made without the sensors 85 and diodes 83, in which case the above-described feedback would be unavailable.

The display screen can also present educational material to the user. The educational material could be related to the subject of dental hygiene, but could also be completely unrelated. For example, the user could take a lesson in French while brushing his or her teeth.

Because the brushes and other moving parts of the toothbrush are encased within the inner shell, these parts can easily be replaced by removing the inner shell from the outer shell, and inserting another inner shell. Thus, the same outer shell and drive motor can be used to power several different toothbrushes. In this way, the toothbrush of the present invention can be used by different persons, each user having an individual set of brushes attached to an individual inner shell.

The toothbrush of the present invention can be powered by a battery, which can be designed to be recharged when the apparatus is not in use. Alternatively, an electric cord can supply power to the motor and/or the display screen.

The toothbrush of the present invention thus enables simultaneous cleansing of the surfaces of substantially an entire arch of the user's teeth. Because the tooth surfaces are cleaned simultaneously, and with powered brushes, the user does a better job of brushing, even if he or she keeps the toothbrush in the mouth only for a short amount of time. Due to the entertainment, educational material, or feedback shown on the display screen, the user is induced to keep the toothbrush in the mouth for a longer time, thus further increasing the quality of the brushing.

The invention is particularly valuable for use with children, who usually need to be prodded to brush properly. The invention is also useful for handicapped or elderly persons, for whom it may be difficult or impossible to use a conventional manual toothbrush. Of course, others who wish to save time in brushing, and/or to monitor their rate of plaque removal, can also benefit from this invention.

The motor used to drive the gears is preferably reversible. One can further improve the quality of the brushing by reversing the direction of the motor periodically, say, every 1000 turns.

The invention is not limited to the gear drive shown in the figures. Other means of driving the brushes can be employed. For example, one could provide an endless, flexible belt which makes each brush rotate. Rotation of the brushes can be induced by friction of the belt against the brushes or their shafts. Alternatively, the belt can include gearlike projections which engage gears attached to the brushes. What is important is that all of the brushes be rotated simultaneously.

The toothpaste used in the brushing operation generally contains a mild abrasive. During the mechanized brushing operation, small particles of abrasive material may enter the gears and may wear them down after repeated use. Therefore, it may be desirable to provide shields (not shown in the drawings) to protect the gears. The shields could assume many forms, and would generally be mounted within the shell, in a manner such that they define partitions which isolate the gears from the brushes.

Other variations in the invention are possible. The configuration and number of the brushes, and their mounting plates, can be changed. The biased hinges which connect the rods to the inner shell can be replaced by springs mounted to the sides of the shell. The connection of the drive shaft to the gears can be changed; the drive shaft could be connected directly to one of the gears 13 instead of being in geared engagement therewith. The housing of the toothbrush can be formed of a single shell. Also, the invention can be practiced with or without the display screen. These modifications, and others which will be apparent to those skilled in the art, should be deemed within the spirit and scope of the following claims.

What is claimed is:

1. An automatic toothbrush for brushing teeth of a user, each of the user's teeth having first and second side surfaces, the toothbrush comprising:
   a) a housing,
   b) a first set of brushes attached to the housing, the brushes of the first set being arranged in a first arc, each brush of the first set being positioned to contact the first side surface of one of the user's teeth, all of the brushes of the first set being rotatable, each brush of the first set having an axis of rotation which is generally perpendicular to said first side surface, the brushes of the first set being connected to each other by a first set of gear means, such that rotation of one of the brushes of the first set causes rotation of all of the brushes of the first set,
   c) a second set of brushes attached to the housing, the brushes of the second set being arranged in a second arc generally parallel to the first arc, each brush of the second set being positioned to contact the second side surface of one of the user's teeth, all of the brushes of the second set being rotatable, each brush of the second set having an axis of rotation which is generally perpendicular to said second side surface, the brushes of the second set being connected to each other by as second set of gear means, such that rotation of one of the brushes of the second set causes rotation of all of the brushes of the second set, at least one member of the first set of gear means being engaged with a member of the set of second gear means, wherein the brushes of the first and second sets are positioned such that a given tooth is contacted on its first side surface by a brush of the first set and on its second side surface by a brush of the second set, and
   d) means for imparting rotation to a member of the first set of gear means.

2. The toothbrush of claim 1, wherein the housing defines an elongated arc, the housing having sides and an interior, and wherein the brushes of the first set are biased towards the interior of the housing.

3. The toothbrush of claim 2, wherein the brushes of the first set define two generally parallel arcs.

4. The toothbrush of claim 1, wherein the housing defines a closed top and an open bottom, the members of the second set of brushes being attached to the top of the housing, the second set of brushes being biased towards the open bottom of the housing.

5. The toothbrush of claim 1, wherein the rotation imparting means is detachable from the housing.

6. The toothbrush of claim 1, wherein the rotation imparting means is connected to a display screen, the display screen being capable of displaying messages or entertainment to a user.

7. The toothbrush of claim 6, wherein the toothbrush includes at least one radiation source and at least one radiation sensor, the radiation source comprising means for directing radiation towards a tooth, the radiation sensor comprising means for detecting radiation reflected from the tooth and for producing a signal indicative of the intensity of reflected radiation, the toothbrush including means for connecting the sensor to the display screen.

8. The toothbrush of claim 1, wherein the brushes of the first set are held within mounting plates, the mounting plates being non-rotatably mounted to the housing, the brushes of the first set being rotatable relative to the mounting plates.

9. The toothbrush of claim 8, wherein the housing has an interior, wherein the mounting plates are affixed to the housing by spring-biased hinges affixed to the housing within the interior of the housing, and wherein the mounting plates tend to urge the brushes of the first set towards the interior of the housing.

10. The toothbrush of claim 1, wherein the housing includes an inner shell and an outer shell, the inner and outer shells being detachably affixed to each other, and wherein the brushes of the first and second sets are affixed to the inner shell and not to the outer shell.

11. The toothbrush of claim 1, wherein each tooth has a top surface, the toothbrush further comprising at least one top brush positioned to contact the top surface of one of the user's teeth, the top brush being connected to one of said first and second sets of brushes such that rotation imparting means also causes rotation of the top brush, wherein the top brush has an axis of rotation which is generally perpendicular to a line joining adjacent teeth of the user.

12. A tooth brushing apparatus comprising a toothbrush having a plurality of brushes capable of simultaneously brushing a plurality of teeth of a user, the brushes being connected to a handle which is connected to a display screen, the display screen comprising means for displaying messages or graphical entertainment to the user while the user is brushing the teeth, the apparatus also including means for storing said messages or graphical entertainment, the storing means being located in the tooth brushing apparatus and being operatively connected to the display screen.

13. The apparatus of claim 12, further comprising means for directing light towards said teeth, and for sensing light reflected from said teeth, the sensing means having an output which is connected to the display screen, wherein the display screen comprises means for providing feedback to the user concerning the efficacy of the brushing operation.

14. An automatic toothbrush for brushing teeth of a user, each of the user's teeth having a side surface, the toothbrush comprising:
   a) a shell,
   b) a set of brushes attached to the shell, said brushes being arranged in an arc, each of said brushes being positioned to contact the side surface of one of the user's teeth, all of said brushes being rotatable, each brush having an axis of rotation which is generally perpendicular to said side surface, the brushes being connected to each other by a set of gear means, such that rotation of one of the brushes causes rotation of all of the brushes, and c) means for imparting rotation to at least one of the gear means.

15. The toothbrush of claim 14, further comprising display means for displaying an image to a user of the toothbrush, the display means being connected to an arm which is affixed to the toothbrush.

16. The toothbrush of claim 15, further comprising a light source and a light sensor, the light source and sensor being mounted to the shell such that light from the light source can reach a tooth of a user, and such that reflected light from the tooth can reach the sensor, the sensor being connected to the display means, wherein the display means comprises means for providing feedback to the user on the efficacy of a brushing operation.

17. The toothbrush of claim 15, wherein the display means includes slot means for receiving a data storage medium.

18. The toothbrush of claim 15, wherein the shell is connected to a handle, and wherein the arm is detachably connected to the handle.

19. The toothbrush of claim 14, wherein each tooth has a top surface, the toothbrush further comprising at least one top brush positioned to contact the top surface of one of the user's teeth, the top brush being connected to one of said brushes which contacts the side surface of the tooth, such that the rotation imparting means also causes rotation of the top brush, wherein the top brush has an axis of rotation which is generally perpendicular to a line joining adjacent teeth of the user.

20. A tooth brushing apparatus comprising a toothbrush having a plurality of brushes capable of simultaneously brushing a plurality of teeth of a user, the brushes being connected to a handle which is connected to a display screen, the display screen comprising means for displaying messages or graphical entertainment to the user while the user is brushing the teeth, the apparatus further comprising means for directing light towards said teeth, and for sensing light reflected from said teeth, the sensing means having an output which is connected to the display screen, wherein the display screen comprises means for providing feedback to the user concerning the efficacy of the brushing operation.

* * * * *